United States Patent
Pulford et al.

(10) Patent No.: US 7,033,319 B2
(45) Date of Patent: *Apr. 25, 2006

(54) ABDOMINAL RETRACTOR

(75) Inventors: John C. Pulford, Groton, MA (US); Marco Pelosi, New Providence, NJ (US)

(73) Assignee: Apple Medical Corporation, Marlboro, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/828,538

(22) Filed: Apr. 20, 2004

(65) Prior Publication Data

US 2004/0260153 A1    Dec. 23, 2004

Related U.S. Application Data

(63) Continuation-in-part of application No. 10/097,421, filed on Mar. 14, 2002, now Pat. No. 6,723,044.

(51) Int. Cl.
*A61B 1/32* (2006.01)
*A61B 19/12* (2006.01)

(52) U.S. Cl. ................ 600/208; 600/201; 128/856

(58) Field of Classification Search ............. 600/205, 600/206, 207, 208, 209, 210, 201, 203; 128/849, 128/850, 851, 852, 853, 854, 855, 856
See application file for complete search history.

(56) References Cited

U.S. PATENT DOCUMENTS

| | | |
|---|---|---|
| 1,196,250 A | 8/1916 | Kuhn |
| 1,810,466 A | 6/1931 | Deutsch |
| 2,305,289 A | 12/1942 | Coburg |
| 2,739,587 A | 3/1956 | Scholl |
| 3,111,943 A | 11/1963 | Orndorff |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,416,520 A | 12/1968 | Creager, Jr. |
| 3,476,109 A | 11/1969 | Hurney |
| 3,523,534 A | 8/1970 | Nolan |
| 3,782,370 A * | 1/1974 | McDonald ............ 600/207 |
| 3,841,332 A | 10/1974 | Treacle |
| 3,863,639 A * | 2/1975 | Kleaveland ............ 128/850 |

(Continued)

FOREIGN PATENT DOCUMENTS

AU    165664    3/1954

(Continued)

OTHER PUBLICATIONS

US 4,777,493, 10/1988, Chvapil (withdrawn)

*Primary Examiner*—Eduardo C. Robert
*Assistant Examiner*—David Comstock
(74) *Attorney, Agent, or Firm*—Kudirka & Jobse, LLP (57) ABSTRACT

An adjustable retractor is disclosed comprising an inner ring, an outer ring spaced from the inner ring, and an elongate sleeve open at opposite ends. The sleeve is provided and extends between the inner and outer rings and is connected at the opposite ends to the rings. The outer ring is provided with a pre-loaded rotational torque to assist with rotation of the outer ring about its central axis to roll the sleeve about the outer ring to adjust sleeve length. An obstetrics version of the retractor may be used for caesarean sections. A hydraulically controlled retractor includes fluid channels in the inner and outer rings that may be dilated by injection of an appropriate fluid.

17 Claims, 7 Drawing Sheets

U.S. PATENT DOCUMENTS

| | | | |
|---|---|---|---|
| 4,043,328 A | 8/1977 | Cawood, Jr. et al. | |
| 4,188,945 A | 2/1980 | Wenander | |
| 4,553,537 A | 11/1985 | Rosenberg | |
| 4,926,851 A | 5/1990 | Bulley | |
| 4,984,564 A * | 1/1991 | Yuen | 600/207 |
| 5,159,921 A | 11/1992 | Hoover | |
| 5,178,133 A | 1/1993 | Pena | |
| 5,263,922 A | 11/1993 | Sova et al. | |
| 5,326,370 A * | 7/1994 | Love et al. | 606/167 |
| 5,342,385 A * | 8/1994 | Norelli et al. | 606/193 |
| 5,366,478 A | 11/1994 | Brinkerhoff et al. | |
| 5,480,410 A | 1/1996 | Cuschieri et al. | |
| 5,514,123 A | 5/1996 | Adolf et al. | |
| 5,520,609 A * | 5/1996 | Moll et al. | 600/204 |
| 5,522,791 A | 6/1996 | Leyva | |
| 5,524,644 A | 6/1996 | Crook | |
| 5,636,645 A | 6/1997 | Ou | |
| 5,640,977 A | 6/1997 | Leahy et al. | |
| 5,649,550 A | 7/1997 | Crook | |
| 5,803,921 A | 9/1998 | Bonadio | |
| 5,853,395 A | 12/1998 | Crook et al. | |
| 5,906,577 A | 5/1999 | Beane et al. | |
| 6,083,155 A * | 7/2000 | Trese | 600/236 |
| 6,382,211 B1 | 5/2002 | Crook | |
| 6,450,983 B1 * | 9/2002 | Rambo | 602/60 |
| 6,582,364 B1 * | 6/2003 | Butler et al. | 600/208 |

FOREIGN PATENT DOCUMENTS

| | | |
|---|---|---|
| FR | 484539 A | 10/1917 |
| GB | 858821 | 1/1961 |
| WO | WO99/03416 | 1/1999 |

* cited by examiner

ABDOMINAL RETRACTOR

RELATED APPLICATIONS

This application is a continuation-in-part of U.S. patent application Ser. No. 10/097,421 now U.S. Pat. No. 6,723,044 filed Mar. 14, 2002 by John C. Pulford and Marco Pelosi, entitled "Abdominal Retractor".

FIELD OF THE INVENTION

The present invention relates generally to surgical retractors, and more particularly to adjustable surgical retractors for use in expanding incisions performed during surgery

BACKGROUND OF THE INVENTION

Abdominal retractors are well known, and are typically used during surgery to expand incisions so that body parts under the incision may be accessed by the surgeon. One well-known type of abdominal retractor is a metal retractor. Metal retractors are typically placed at opposite sides of the incision to expand the incision for surgery. Metal retractors have often been used with cotton sponges held against the sides of the incision by the retractors.

Other types of retractors include wound edge protectors. Examples of wound edge protectors include those shown in U.S. Pat. Nos. 3,347,226 and 3,347,227. However, these wound edge protectors do not adjust the vertical length of the sleeve. Wound edge protectors typically have an inner ring spaced from an outer ring with a flexible sheet of material formed into a sleeve extending between the rings and connected at opposite ends to the rings. During surgery, the inner ring is squeezed into an oblong shape to be inserted through the wound and to be allowed to expand against the inside edge of the wound. The outer ring overlaps the outside edge of the wound to cause the sleeve to contract the sides of the wound and expand the wound for surgery. The sides of the wound are also protected by the sleeve from contamination during surgery. These wound edge protectors are typically not adjustable and numerous different sized retractors are required having varying sized rings and/or sleeve lengths for different sized wounds.

In another known wound edge protector, the circumference of the wound edge protector is adjustable by use of telescoping inner and outer rings and overlapping lengthwise sleeve edges.

Also known is an incision liner and retractor which is similar in construction to wound edge protectors. In the incision liner and retractor, the length of the sleeve is incrementally adjustable by rolling the sleeve onto the circumference of the outer ring by rotating the outer ring about its central axis. In one example, the outer ring has an oblate cross-section with opposed flat chordal surfaces to assist in rotating the ring about its central axis. However, manually rotating the outer ring about its central axis is often difficult. An example of such an incision liner and retractor is found in U.S. Pat. No. 5,524,644.

SUMMARY OF THE INVENTION

In one aspect of the invention, an adjustable retractor is disclosed. The adjustable retractor comprises an inner ring, an outer ring spaced from the inner ring, and an elongate sleeve open at opposite ends. The sleeve extends between the inner and outer rings and is connected at its opposite ends to the inner and outer rings. The outer ring is provided with a pre-loaded rotational torque to assist with rotation of the outer ring about its central axis to roll the sleeve about the outer ring to adjust sleeve length.

According to one embodiment, the outer ring is formed in a mobius configuration to provide the pre-loaded rational torque of the outer ring. In the mobius configuration, an outer circumference is rotationally offset or twisted by a predetermined amount about the central axis of the outer ring along the length of the ring. The outer ring may Include a tube having two ends secured together, the circumferences of the ends being offset from one another. The offset may be gradual, proceeding longitudinally along the central axis of the outer ring. In another embodiment, the offset may be discontinuous or occur in at least one step. According to another embodiment, the circumference is offset at least about 20° about the central axis of the outer ring. The circumference may be offset between about 45° and about 540° about the central axis of the outer ring. In another embodiment, the predetermined amout of the offset may be about 180° or about 360°.

In another embodiment, the cross-section may be shaped in numerous different configurations including substantially circular, substantially star-shaped having at least four points, substantially parallelogram, substantially polygonal, or substantially cruciform.

According to another embodiment, the one location has a cross-sectional shape that matches a cross-sectional shape at the other location. The outer circumference of the outer ring at the one location may be offset with respect to the outer circumference at the other location about the central axis of the outer ring by an amount to match the cross-sectional shape at the one location with the cross-sectional shape at the other location. The outer circumference of the cross-section at the one location may be offset 180° about the central axis of the outer ring to with respect to the outer circumference at the other location.

According to another embodiment of the invention, in operation the entire outer ring is rotatable manually about its central axis. The sleeve may be a thin, flexible sheet having overlapping sealed edges to form a cylinder. In yet another embodiment, the sleeve may be seamless. The opposite ends of the sleeve may be wrapped about the rings and secured to the sleeve. The inner ring may be squeezable into an oblong shape for insertion into a surgical incision and may be constructed to return to its original shape when released to bear against an inner edge of a surgical incision. Length of the sleeve may be adjustable to locate the outer ring against an outer edge of a surgical incision. The length of the sleeve may be adjustable before or after insertion of the inner ring into a surgical incision.

In another embodiment of this aspect of the invention, an adjustable retractor comprises an inner ring squeezable into an oblong shape for insertion into a surgical incision and structured to return to its original shape to bear against an inner edge of the surgical incision. An outer ring is spaced from the inner ring, the outer ring being formed in a mobius configuration. A sleeve having two ends extends between the inner and outer rings. The inner and outer rings are secured to the opposite ends of the sleeve. The outer ring in operation is rotatable about its central axis to roll the sleeve about itself and the outer ring and thereby adjust sleeve length to locate the outer ring adjacent an outer edge of the surgical incision.

In one embodiment, the outer ring has a cross-sectional shape, the mobius configuration may include one location on an outer circumference of the outer ring rotationally offset with respect to another location by a predetermined amount about the central axis of the outer ring. The offset may be gradual, proceeding longitudinally along the central axis of the outer ring. In another embodiment, the offset may be discontinuous or occur in at least one step. The outer circumference may be offset at least about 20° about the central axis of the outer ring. In another embodiment, the outer circumference may be offset between about 45° and about 540° about the central axis of the outer ring. The one location may have a cross-sectional shape that matches a cross-sectional shape at the other location. The outer circumference of the outer ring at the one location may be offset with respect to the outer circumference at the other location about the central axis of the outer ring by an amount to match the cross-sectional shape at the one location with the cross-sectional shape at the other location. The outer circumference of the cross-section at the one location may be offset 180° about the central axis of the outer ring to with respect to the outer circumference at the other location. The outer ring may have a cross-sectional shape in numerous different configurations.

In yet another aspect of the invention, a method of adjusting a retractor is disclosed. The method comprises the steps of: providing an inner and an outer ring spaced apart from one another, providing an elongate sleeve extending between the inner and outer rings, the sleeve having a length and two opposed ends, each end being secured to one of the inner and outer rings, providing a pre-loaded rotational torque on the outer ring, and adjusting the length of the sleeve by rotating the outer ring about its central axis with the assistance of the pre-loaded torque to roll the sleeve about itself and the outer ring to adjust sleeve length. According to one embodiment, the outer ring is formed in a mobius configuration to provide the pre-loaded rotational torque on the outer ring.

In one embodiment of the invention, a version of the retractor is specifically configured for use in an obstetrics application, particularly a caesarean section. The adjustable retractor of this embodiment uses an inner ring and an outer ring, and an elongate sleeve open at opposite ends, as with other embodiments. However, in this embodiment, the size of each ring of the retractor is significantly larger than in other embodiments, so as to accommodate the head of a newborn baby. The outer ring may still make use of a pre-loaded rotational torque that assists with the rotation of the outer ring about its central axis. In practice, a smaller incision is made in the abdomen than might typically be necessary, and the inner ring of the retractor is inserted into the incision. The sleeve is then rolled around the outer ring to expand the incision to a roughly circular shape. After delivery of the baby, the sleeve is unrolled from the outer ring, and the inner ring is removed from the wound.

In still another embodiment of the invention, an adjustable retractor is provided that has an inner ring with a fluid-tight channel into which a fluid may be transferred to dilate the inner ring. Similarly, an outer ring is provided that is spaced apart from the inner ring and that has a fluid-tight channel into which a fluid may be transferred to dilate the outer ring. An elongate sleeve is provided that is open at opposite ends and that extends between the inner and outer rings. The sleeve is connected at opposite ends to the rings. Each of the inner and outer rings may also include a radial support, such as a garter spring, that is located adjacent to its respective fluid channel and provides a radial force to the fluid channel in an undilated state. In one version of this embodiment, the sleeve itself is sealed to itself to form the fluid tight channel. In another version, a fluid tube is located within a cavity of the radial support, and expands the radial support upon dilation.

BRIEF DESCRIPTION OF THE DRAWINGS

The above and further advantages of the invention may be better understood by referring to the following description in conjunction with the accompanying drawings in which.

DETAILED DESCRIPTION

Figure 1:
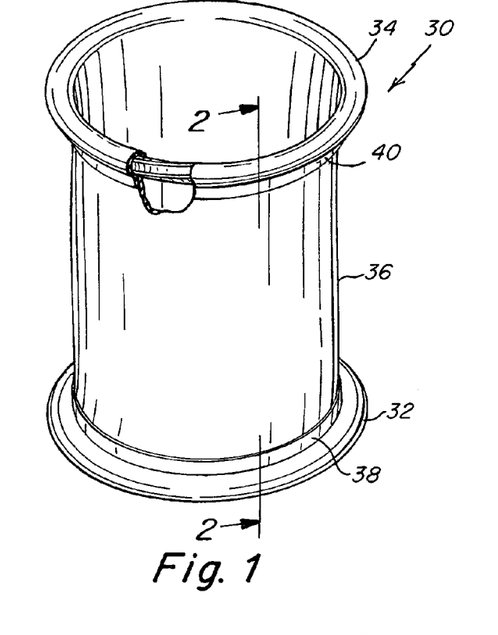
FIG. 1 is a partially broken-away perspective view of one embodiment of a retractor according to the present invention, in a fully extended state.
Figure 2:
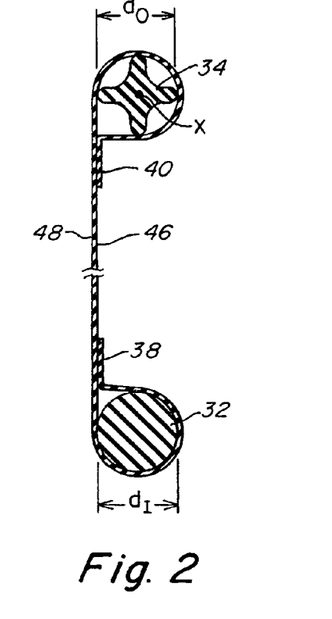
FIG. 2 is a cross-sectional view of the retractor of FIG. 1 taken along line 2—2 of FIG. 1.

With reference now to the drawings, and more particularly to FIGS. 1 and 2 thereof, one aspect of this invention features a retractor 30. Retractor 30 includes an inner ring 32 and an outer ring 34 spaced from inner ring 32. An elongate sleeve 36 having two opposed ends 38 and 40 is provided and extends between inner and outer rings 32 and 34. One opposed end 38 is secured to inner ring 32 and the other end 40 is secured to outer ring 34.

In one embodiment of the invention, sleeve 36 is a flexible tubular sheet having a substantially uniform circumference between ends 38 and 40. Preferably, the sleeve is nonflammable, physiologically inert, substantially impermeable to fluid and bacteria, and resistant to melting. In one embodiment, sleeve 36 is made of a polyurethane thin film, although other suitable materials may be used, such as polyolefins. The sleeve material may be substantially transparent and may have any desired color. Sleeve 36 may be produced in any suitable manner, for example in a seamless tubular form, or by a flat sheet which is formed into a tubular shape and in which the longitudinal edges of the sleeve are overlapped and sealed to one another. Sleeve 36 may have any desired length L when secured to inner and outer rings 32 and 34; however, its length will depend on the type of surgeries to be performed with retractor 30. It is preferable that the sleeve length L be long enough to accommodate incisions having walls of different thickness IwT. Diameter Ds of sleeve 36 will also vary depending on the size of the incision used in the surgeries to be performed with retractor 30.

As shown in FIGS. 2 and 5–7, inner ring 32 typically has a substantially round cross-sectional shape. It will be appreciated, however, that the cross-sectional shape of the inner ring may be any desired configuration. Furthermore, the cross-sectional shapes of inner and outer rings 32 and 34 may be the same or different. The cross-sectional shape of inner ring 32 has a particular diameter $d_I$. Diameter $d_I$ may be any suitable length; however, the length selected will depend on a number of factors, including at least overall diameter $D_I$ of inner ring 32, the material selected, and the cross-sectional shape of inner ring 32. Inner ring 32 is preferably capable of being squeezed into a substantially oblong shape for insertion into an incision, and is capable of returning back to its original shape, for example after insertion into the body. As shown, inner ring 32 has a substantially circular shape. However, it will be appreciated that inner ring 32 may have any other suitable shape, for example oval. Inner ring 32 may be formed in any suitable manner. For example, inner ring 32 may be molded as one-piece or inner ring 32 may be formed of a length of tube having two ends, with the ends being secured together.

As shown in FIGS. 1 and 2, opposed ends 38 and 40 of sleeve 36 are secured to inner and outer rings 32 and 34, respectively. As shown in FIG. 2, opposed ends 38 and 40 of sleeve 36 are preferably wrapped about respective rings 32 and 34 at least once and are then secured, such as by heat sealing sleeve 36 to itself. Preferably, opposed ends 38 and 40 are secured to outside surface 46 of sleeve 36. It will be appreciated that sleeve 36 may be secured in any other suitable manner to inner and outer rings 32 and 34. For example, opposed ends 38 and 40 may be wrapped around the rings 32 and 34 and secured to inside surface 48 of sleeve 36.

Figure 3:
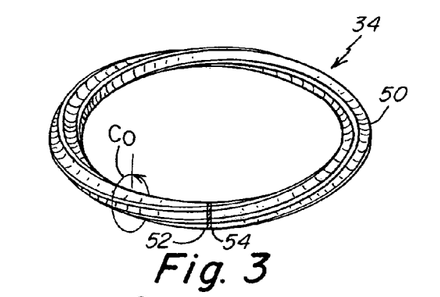
FIG. 3 is a perspective view of one embodiment of an outer ring according to 30 the invention.
Figure 4:
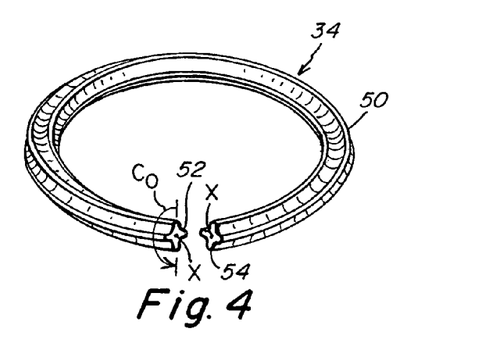
FIG. 4 is a perspective view of another embodiment of an outer ring according to the invention.

Referring now to FIGS. 2–4, outer ring 34 has a size which is substantially similar to that of inner ring 32. Outer ring 34 may have almost any desired cross-sectional shape, as described in further detail below. Outer ring 34 has a central axis X as shown in FIG. 2 that extends through the cross-sectional center of outer ring 34 along its entire length. The cross-sectional shape has a largest diameter do, and may be any desired length. However, the length selected will depend on a number of factors, including at least overall diameter $D_o$ of outer ring 34, the material selected, and the cross-sectional shape of outer ring 34. Outer ring 34 is configured so that outer circumference C thereof may be rotated about its central axis X. As shown in FIGS. 1, 3 and 4, outer ring 34 has a substantially circular shape. However, it will be appreciated that outer ring 34 may have any other suitable shape, for example oval.

This mobius configuration of outer ring 34 pre-loads outer ring 34 with rotational torque, such that the offset Co facilitates rotation of outer ring 34 about its central axis X. Outer ring 34 may be turned either outwardly or inwardly, but once outer ring 34 is partially rotated about its central axis X the remainder of outer ring 34 will tend to rotate on its own to complete the twisting motion because of the pre-loaded rotational torque.

Outer ring 34 may have any desired cross-sectional shape. Particular cross-sectional shapes will be discussed below for exemplary purposes only. In one example, as shown in the embodiment of FIGS. 1–7, outer ring 34 has a substantially cruciform cross-sectional shape. Generally, the cruciform cross-sectional shape includes a circle from which four regularly spaced circular arcs of a somewhat larger radius have been excised, resulting in a cross-sectional shape formed of eight circular segments that are alternately concave and convex.

Figure 8:
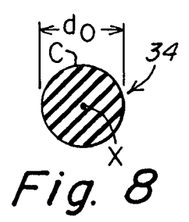
FIG. 8 is a cross-sectional view of another embodiment of the outer ring according to the invention.

In another example, as shown in FIG. 8, outer ring 34 may have a substantially circular cross-sectional shape. The circumference of FIG. 8 may be offset by any desired amount Co about the central axis X of the outer ring 34. However, it will be understood that a greater amount of offset will make the outer ring easier to rotate about its central axis X by providing more pre-loaded torque, while too much offset will also not be optimal.

Figure 9:
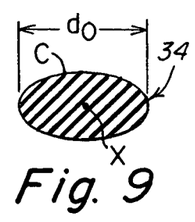
FIG. 9 is a cross-sectional view of yet another embodiment of the outer ring according to the invention.
Figure 10:
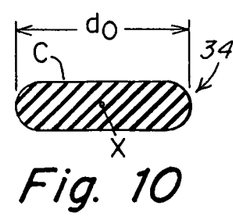
FIG. 10 is a cross-sectional view of yet another embodiment of the outer ring according to the invention.
Figure 11:
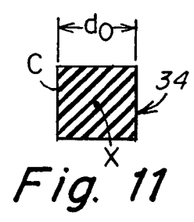
FIG. 11 is a cross-sectional view of yet another embodiment of the outer ring according to the invention.
Figure 12:
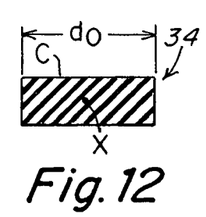
FIG. 12 is a cross-sectional view of yet another embodiment of the outer ring according to the invention.

Referring now to FIGS. 9 and 10, other exemplary cross-sectional shapes for outer tube 34 are illustrated. FIG. 9 shows an elliptical cross-sectional shape, while FIG. 10 shows an oblate cross-sectional shape having flat chordal surfaces opposite one another. Either of these cross-sectional shapes may be offset or rotated in multiples of 180° about the central axis X of outer ring 34 so that matching portions of the circumference are matched with one another. However, it will be appreciated that the circumference may be offset by any desired amount $C_o$, as the matching portions thereof do not need to mate with one another.

Figure 13:
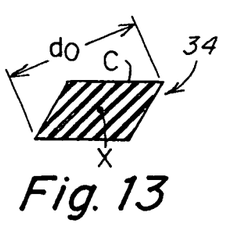
FIG. 13 is a cross-sectional view of yet another embodiment of the outer ring according to the invention.
Figure 14:
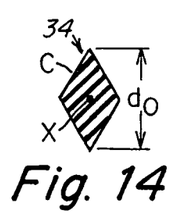
FIG. 14 is a cross-sectional view of yet another embodiment of the outer ring according to the invention.
Figure 15:
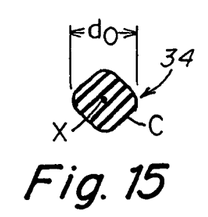
FIG. 15 is a cross-sectional view of yet another embodiment of the outer ring according to the invention.

FIGS. 11–15 show various parallelogram cross-sectional shapes that could be used for outer ring 34. These parallelogram cross-sectional shapes include a square (FIG. 11), a rectangle (FIG. 12) and a diamond (FIGS. 13 and 14). Each has a largest cross-sectional dimension, $d_o$. It will be appreciated that corners of the cross-sectional shapes may be rounded or pointed. It will also be appreciated that the circumferences may be offset by any desired amount Co about the central axis X of the outer ring 34. For example, the circumference of FIG. 11 may be rotationally offset a quarter turn (90°), a half-turn (180°), a three-quarter turn (270°), a full turn (360°) or multiples of thereof, such that the circumferences of locations 52 and 54 mate with one another on outer ring 34 in a seamless manner. However, it will be appreciated that the circumference may be offset about the central axis X of outer ring 34 by an amount that does not align the cross-sectional shapes of locations 52 and 54 in a seamless manner.

Figure 16:
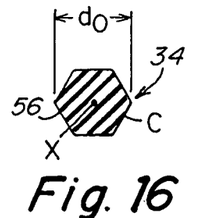
FIG. 16 is a cross-sectional view of yet another embodiment of the outer ring according to the invention.

FIG. 16 shows a polygonal cross-sectional shape having six sides or a hexagonal cross-sectional shape. It will be understood that a polygonal cross-sectional shape may have any number of sides 56. Once again, the circumference may be rotationally offset by a desired amount about the central axis X of outer ring 34, such that matching portions of the cross-sectional shape mate with one another at locations 52 and 54 or such that they do not mate with one another at locations 52 and 54. In order to determine the amount to offset the circumference to mate matching cross-sectional portions at locations 52 and 54, the circumference may be offset by 360° divided by the number of sides 56 of the polygon, or multiples thereof.

Figure 17:
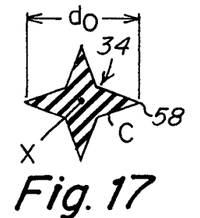
FIG. 17 is a cross-sectional view of yet another embodiment of the outer ring according to the invention.
Figure 18:
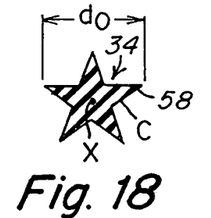
FIG. 18 is a cross-sectional view of yet another embodiment of the outer ring according to the invention.
Figure 19:
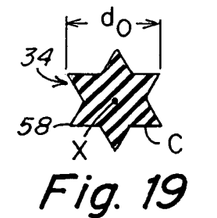
FIG. 19 is a cross-sectional view of yet another embodiment of the outer ring according to the invention.
Figure 20:
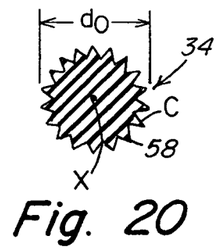
FIG. 20 is a cross sectional view of yet another embodiment of the outer ring according to the invention.

FIGS. 17–20, show star cross-sectional shapes for outer ring 34. It will be understood that a star cross-sectional shape having any number of points 58 may be used. For the purposes of illustration only, FIG. 17 shows a star with four points 58, FIG. 18 shows a star with five points 58, FIG. 19 shows a star with six points 58, and FIG. 20 shows a star with 18 points 58. Moreover, it will be understood that the circumference may be rotationally offset about the central axis X of outer ring 34, by the number of points 58 divided by 360° or multiples thereof to mate matching points 58 of the star at locations 52 and 54. For example, the four point star may be offset by 90°, 180°, 270° and 360° or multiples thereof, while the eighteen point star may be offset by any increment of 20° (360° divided by the 18 points of the star). Of course, as before it will be appreciated that it is not necessary to mate matching points 58 of the stars with one another when the circumference is offset about the central axis X of outer ring 34.

Figure 21:
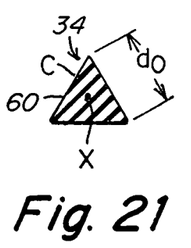
FIG. 21 is a cross-sectional view of yet another embodiment of the outer ring according to the invention.

FIG. 21 shows a triangular cross-sectional shape for outer ring 34. The triangular cross-sectional shape may have sides 60 of equal or unequal length. In one embodiment, for an equilateral triangle, the circumference may be offset about the central axis X of outer ring 34 by 120°, 240° and 360°, or multiples thereof to mate matching sides of the triangular cross-sectional shape with one another at locations 52 and 54. Of course, it will be appreciated that the circumference may be offset by an amount that does not mate the sides of the triangular cross-sectional shapes with one another at locations 52 and 54.

Figure 22:
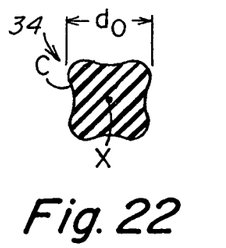
FIG. 22 is a cross-sectional view of yet another embodiment of the outer ring according to the invention.
Figure 23:
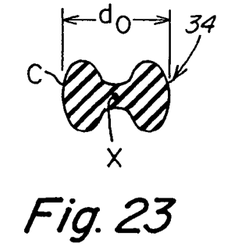
FIG. 23 is a cross-sectional view of yet another embodiment of the outer ring according to the invention.

FIG. 22 shows another embodiment of the cruciform cross-sectional shape of FIGS. 1–7. FIG. 23 shows a dog-bone cross-sectional shape. It will be appreciated that the circumference of these figures may be offset by any desired amount $C_o$ at locations 52 and 54, as described above It will also be understood that any of the cross-sectional shapes described above or other possible cross-sectional shapes may be irregular, such as a rhombus shaped cross-section. It will also be understood that the examples of cross-sectional shapes illustrated above are not intended to limit the invention disclosed herein and that many other possible shapes for outer ring 34 may be used in accordance with this invention.

Inner and outer rings 32 and 34 are preferably made of a medical grade polyurethane material. In one embodiment, the material of inner and outer rings 32 and 34 has between about 70 and about 90 durometer, Shore A. It will be understood that any other suitable material could be used, such as polyethylene or polypropylene. The material of inner and outer rings 32 and 34 may be the same or different. The material of inner ring 32 will preferably allow inner ring 32 to be squeezed into an oblong shape for insertion into the incision and still return to its original shape when inner ring 32 is in place against an inner edge 42 of the incision. The material of outer ring 34 will preferably allow the circumference of outer ring 34 to be rotated about its central axis X using a thumb and fingers and still allow outer ring 34 to be stable when located against an outer edge 44 of the incision.

Inner and outer rings 32 and 34 have respective diameters $D_I$ and $D_o$ that may vary depending on the size of the incision to be used with retractor 30. Generally, the greater the diameter of the rings, the greater is the durometer of the preferred material, while the smaller the diameter, the lower is the durometer of the preferred material. Of course, it will be appreciated that the durometer of the material would change less for small incremental changes in diameter of rings 32 and 34 (i.e. on the order of 20 mm). Also, diameters $D_I$ and $D_o$ of inner and outer rings 32 and 34 and diameter $D_s$ of sleeve 36 are preferably substantially similar, although they could be different from one another. Inner and outer rings 32 and 34 may be different colors. For example, inner ring 32 may be red, while outer ring 34 may be substantially transparent.

Figure 5:
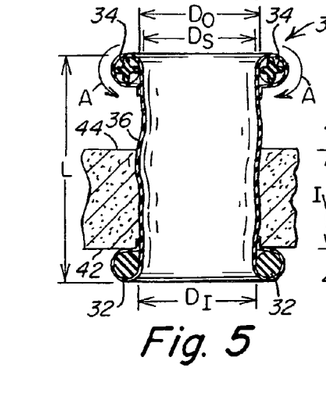
FIG. 5 is a cross-sectional schematic view of the retractor of FIG. 1 partially installed in a surgical incision.
Figure 6:
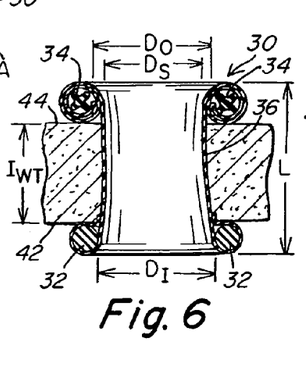
FIG. 6 is a cross-sectional schematic view of the retractor of FIG. 5 completely installed in the surgical incision.
Figure 7:
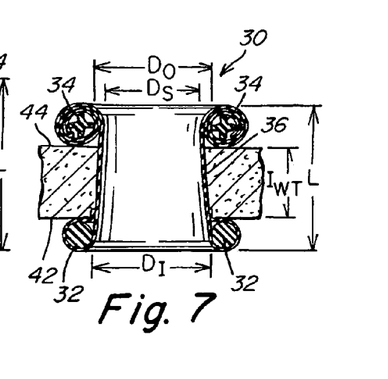
FIG. 7 is a cross-sectional schematic view of the retractor of FIG. 1 completely installed in a surgical incision having a thinner wall than the incision of FIGS. 5 and 6.

The mobius configuration of outer ring 34 described above facilitates the rolling and unrolling of sleeve 36 onto outer ring 34 to adjust sleeve length L. One illustrative method of adjusting sleeve length L according to the invention, will now be discussed. To shorten the length L of sleeve 36, a thumb and forefinger of each hand may be placed on outer ring 34 of retractor 30. For example, the left hand may be placed at about the 10 o'clock position and the right hand may be placed at about the 2 o'clock position on outer ring 34. The outer surface of outer ring 34 is grasped by each hand and outer ring 34 is rotated or turned outwardly about central axis X away from sleeve 36 in the same (i.e. at the 10 and 2 o'clock) direction, as shown in FIG. 5 by the direction of arrows A. Once part of outer ring 34 about central axis X is rotated outwardly the remainder of outer ring 34 will continue to rotate outwardly about central axis X until all of outer ring 34 has been rotated a full turn (i.e. about 360°) about its central axis X, because of the pre-loaded torque caused by the mobius configuration. As outer ring 34 is rotated outwardly about its central axis X, the sleeve 36 is rolled onto outer ring 34 thereby shortening its length L. Thus, retractor 30 may be used on incisions having a different wall thickness IWT as shown in FIGS. 6 and 7. The incision of FIG. 6 has a greater wall thickness IWT than that of FIG. 7, yet the same retractor 30 may be used to expand both incisions for surgery. Sleeve 36 in either case may be drawn tight against the wall to expand the incision for surgery.

Sleeve 36 may be lengthened in much the same manner after being shortened by rotating or turning outer ring 34 in the opposite direction or inwardly. Once again, as part of outer ring 34 is rotated inwardly, the remainder of outer ring 34 will continue to rotate inwardly until outer ring 34 has been rotated a full turn (i.e. about 360°) about its central axis X. As outer ring 34 is rotated inwardly about its central axis X, sleeve 36 is unrolled from outer ring 34, hereby lengthening the sleeve length L.

It will be appreciated that one or two hands may be used to rotate or turn outer ring 34 outwardly or inwardly thereby using the pre-loaded torque of outer ring 34 resulting from the mobius configuration to facilitate the rotation of outer ring 34. It will also be understood that outer ring 34 could be rotated inwardly to shorten sleeve 36 and rotated outwardly to lengthen sleeve 36. Moreover, it will be appreciated that a separate device may be used to assist in rotating outer ring 34 outwardly or inwardly to roll or unroll sleeve 36 on outer ring 34. For example, a device could be provided on the outer circumference of outer ring 34 to follow one of its surfaces, in either a clockwise or counter-clockwise direction, and cause the surface to always be located on the outside circumference thereby rotating the ring outwardly or inwardly about its central axis to shorten or lengthen the sleeve length.

As described in U.S. Pat. No. 5,524,644, retractor 30 of the present invention may be used during surgery. In one example, retractor 30 may be used in a minimally invasive abdominal surgical procedure. The abdomen is routinely prepared with antiseptic and dried; the site for the incision is traced on the abdomen and covered with a surgical drape; and a muscle split or incision is made at the site through the peritoneum. Retractor 30 is placed though the incision by squeezing inner ring 32 into an oblong shape and inserting it lengthwise through the incision and letting it return to its original shape inside the peritoneum around the inner edge 42 of the incision. Outer ring 34 may be gripped by the thumb and forefinger of both hands and rotated outwardly (as shown in FIG. 5 and discussed above), rolling sleeve 36 onto outer ring 34 until outer ring 34 abuts the outer edge 44 of the incision, as shown in FIGS. 6 and 7. The part of sleeve 36 in the incision between inner and outer rings 32 and 34 is thereby drawn into contiguous contact with the sides of the incision to expand the incision for surgery and provide a self-retaining, protective barrier for surgery. If desired, retractor 30 may be pre-adjusted prior to insertion, or partially pre-adjusted prior to surgery. The mobius configuration of outer ring 34 facilitates rotation of outer ring 34 about its central axis X to shorten or lengthen sleeve 36 by rolling or unrolling the sleeve on or off the outer ring. The mobius configuration also assists in keeping outer ring 34 from unrolling during surgery after the outer ring is in place adjacent the outer edge 44 of the incision.

One specific embodiment of the retractor is directed not only to corrective surgical applications, but to retraction in obstetrics and, in particular, during the delivery of a baby via caesarean section. The obstetrics retractor is considerably larger than those used in the surgical applications described above, as it must retract a region wide enough to allow the passage of a baby's head. This is distinctly different from other surgical applications, in which the diameter was dictated primarily by the space necessary for passage of a surgeon's hands and tools. A general method of using the retractor in this embodiment is described below in conjunction with FIGS. 24A–24C.

After administering anesthesia, an abdominal incision is made by the surgeon above the uterus. While, in a conventional caesarean section, the incision might be rather large (as long as 18–20 cm), the ability of the retractor 63 to open the incision to a wide, nearly circular, profile, allows the length of the incision in the present embodiment to be shorter, on the order of 15 cm. The retractor 63, in this embodiment, may be on the order of 25 cm, and is placed though the incision as described above, by squeezing the inner ring (not shown) into an oblong shape and inserting it lengthwise through the incision and letting it return to its original shape inside the peritoneum around the inner edge of the incision. The outer ring 65 is then rotated to cause the sleeve 67 to expand the incision, the expansion being sufficient to allow not only access to the uterus, but to allow passage of the baby 69 to be delivered.

Figure 24A:
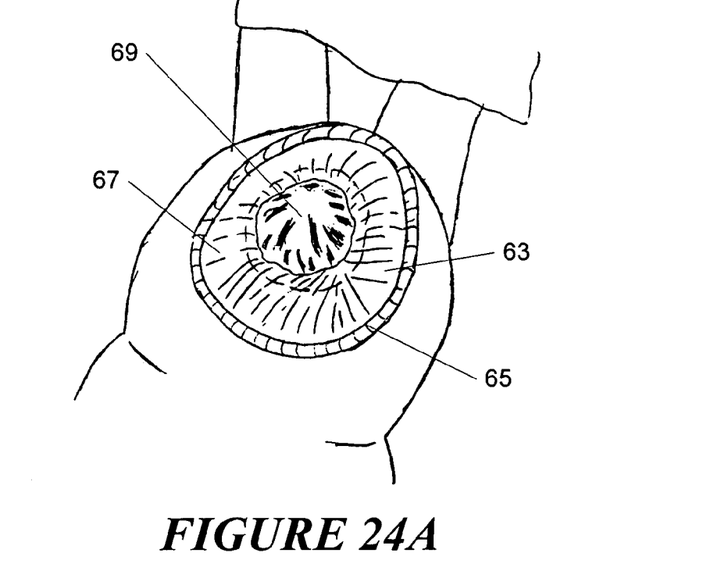
FIGS. 24A–24C are depictions of an obstetrics embodiment of the invention used during a caesarean section.
Figure 24B:
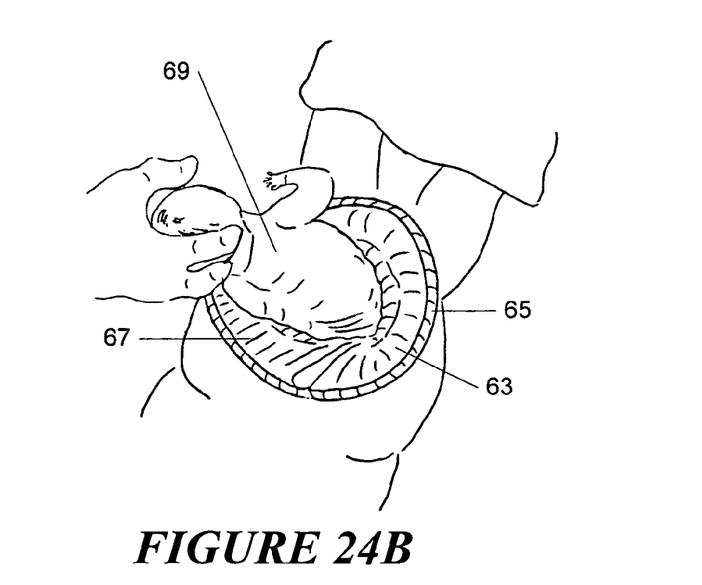
Figure 24C:
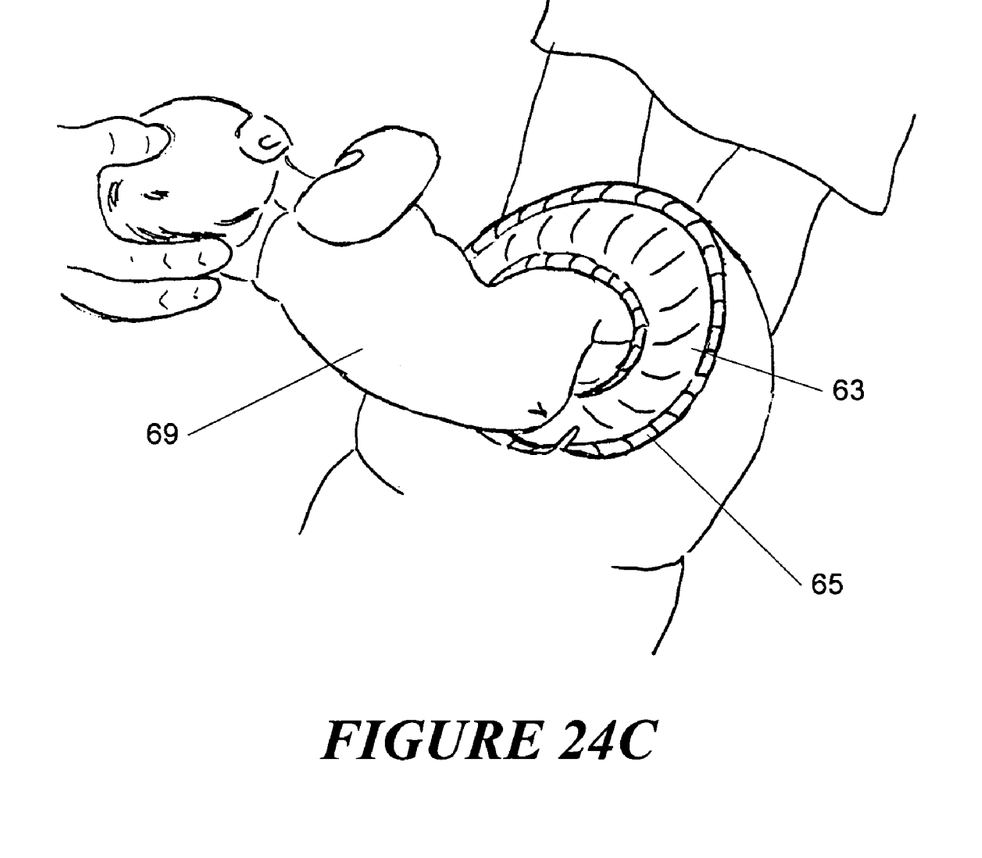

Once the incision is opened, further surgical procedures typical of a caesarean section are performed, including making an incision in the uterus. Once the baby is exposed, the surgeon removes the baby from the uterus, and through the retractor. FIG. 24A shows the top of the head of the baby 69 beginning to protrude through the opening of the retractor 63 (for clarity, surgical dressings and surgeons hands are omitted from the drawing). In FIG. 24B, the baby 69 is shown partially delivered, while in FIG. 24C, the baby 69 is shown almost fully delivered. Care of the baby and necessary surgical repair for the mother then proceeds as normal. The retractor is thereafter removed by unrolling the sleeve 67, squeezing the inner ring into an oblong shape, and withdrawing it from the incision. The incision is thereafter closed as typical to the procedure.

Figure 25:
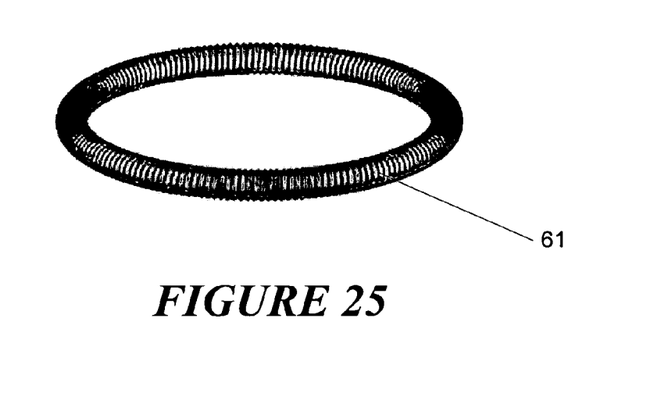
FIG. 25 is a perspective view of a garter ring used with a hydraulically controllable retractor according to the present invention.

In another alternative embodiment of the invention, a different structure is used for the inner ring and the outer ring of the abdominal retractor. While the embodiments described above make use of a solid material for each of the inner and outer rings, a dilatable ring may also be used. The dilatable portion of the ring may be either a portion of the sleeve itself, or a separate fluid tube located within the sealed portion of the sleeve. In each case, it may be desirable to also include a support mechanism for the dilatable ring. Shown in FIG. 25 is a schematic perspective view of a garter spring 61 that may be used to support a dilatable ring of the retractor. The spring 61 may be a helical extension or compression spring whose ends are connected so that the spring becomes a circle and exerts radial forces. In the case where the fluid channel is a portion of the sleeve itself, the spring 61 is simply located within that channel. Where there is a separate fluid tube, the tube may be located within the cavity of the spring 61.

Unlike a solid ring, as is used in the embodiments above, the dilatable ring will change in diameter when a fluid is coupled into its fluid-tight chamber. Thus, when the ring is not filled with fluid (i.e., is "undilated"), the outer diameter of the ring is defined by the diameter of the internal spring when fully relaxed. The radial forces of the spring 61 are sufficient to maintain the circular geometry of the spring throughout the range of dilation, as the fluid channel is filled with fluid and the ring expands significantly in diameter.

Figure 26:
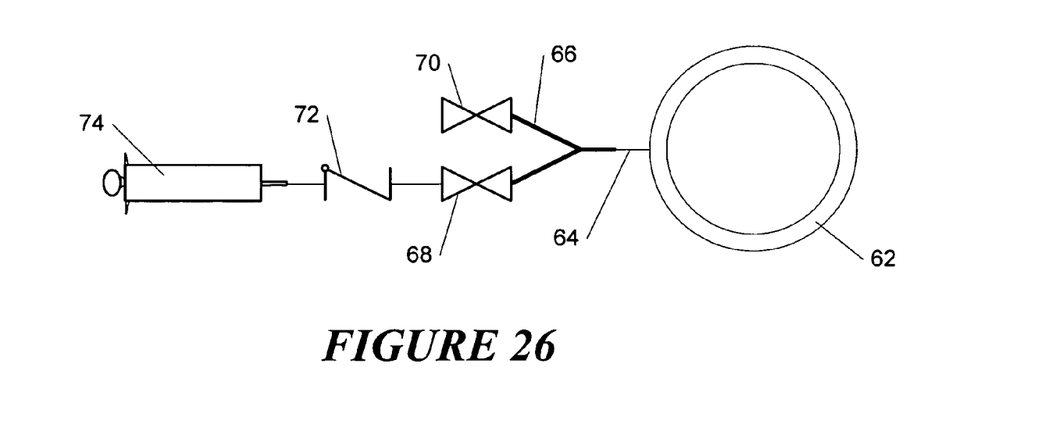
FIG. 26 is a schematic view of components used with the hydraulically controllable retractor.

An example on how the rings may be dilated is depicted schematically in FIG. 26. A ring 62, which may contain a spring 60 such as that shown in FIG. 25, has a fluid port 64 that is connected to a "Y-connector" 66, that is, a two-to-one fluid junction. The two other ports of the connector 66 are connected, respectively to input valve 68 and output valve 70. Each of the valves 68, 70 has a valve control that is easily manipulated by hand, allowing adjustment by a surgeon or assistant. The input valve 68 is, in turn, in fluid communication with a check valve 72, which is fed by a pressurizable source of fluid such as, for example, syringe 74.

For each of the inner ring and the outer ring of the retractor, the rings begin in the non-dilated state. Thus, both rings begin in a very pliable condition. Once the incision is made, the inner ring is easily inserted into the wound. At this time, both valves 68, 70 are closed, and the syringe 74 is filled with a fluid, such as saline solution. The input valve 68 is then opened, and the syringe is compressed to force fluid through the check valve 72 and the input valve 68, and into fluid channel of the ring 62. The fluid causes the ring to dilate, expanding the cross-sectional size as well as the overall diameter of the ring. Once the inner ring has reached the desired diameter, the input valve 68 is closed. The process is then repeated for the outer ring, which uses an identical arrangement as that shown in FIG. 26.

Upon dilation of the two rings, the sleeve between the rings is pulled outward, opening the incision. With the solid ring embodiments described above, the sleeve is longer than necessary, to allow rolling of the outer ring to shorten the effective length of the sheet and thereby open the incision. However, since the rings in the present embodiment begin at a relatively small diameter, the sleeve may be much shorter in overall length. The dilation of the rings may then be used to open the wound, since the more the rings are dilated, the further outward the sleeve is pulled. Since the sleeve material will typically have only limited elasticity, it will still be fabricated as a cylinder with a diameter equal to the fully dilated diameter of the ring. Thus, if the ring has a three-inch diameter at rest, but a ten-inch diameter when fully dilated, the sleeve will be a ten-inch diameter cylinder. Due to the limited elasticity of the sleeve, it is also necessary to ensure that the heat sealed portions of the sleeve at the rings are sufficient for the maximum ring diameters.

With an arrangement as shown in FIG. 26, once the surgical procedure is complete, the retractor may be easily removed by first undilating the outer ring. This is accomplished by opening valve 70 and allowing the hydraulic lock to be vented and the compressive forces of the garter spring to force the ring to return to its undilated diameter. The fluid may also be withdrawn through the valve using a syringe or other device capable of drawing a small vacuum to force the fluid out. Once the outer ring is undilated, the incision partially closes, as the expansive forces of the sleeve are reduced. The inner ring is then undilated, allowing it to be easily withdrawn through the incision, and the final surgical steps are completed. It is also possible to undilate only the inner ring before removal of the retractor, and to undilate the outer ring at a later time.

Figure 27A:
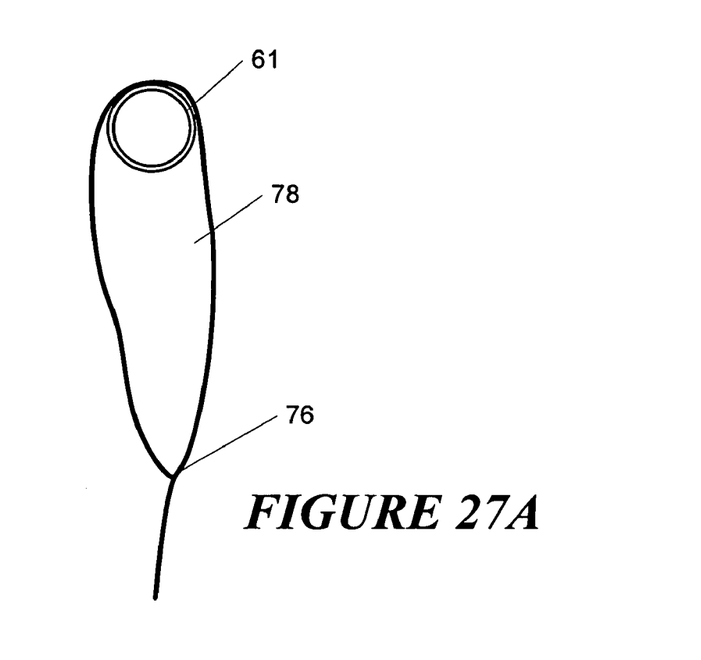
FIGS. 27A and 27B are schematic cross-sectional views of a dilatable ring used with the hydraulically controllable embodiment of the invention shown, respectively, in undilated and dilated states.
Figure 27B:
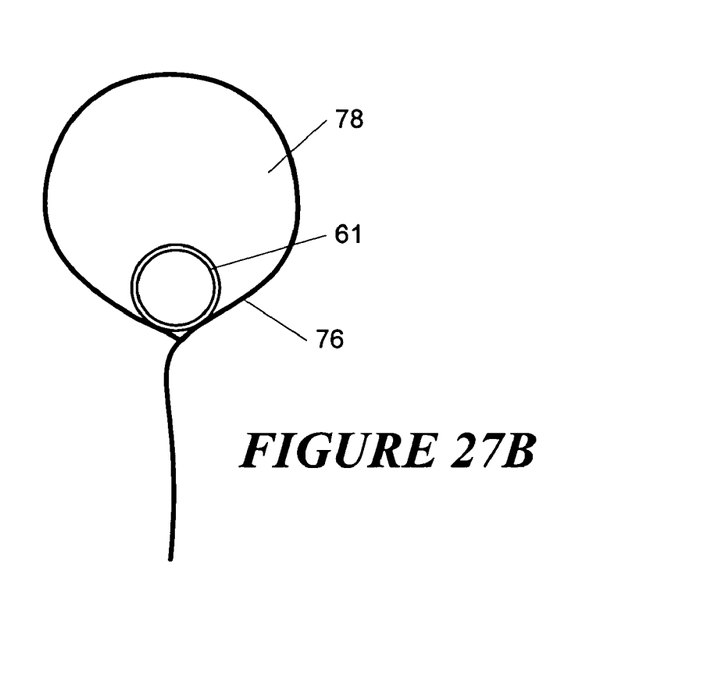

Shown schematically in FIGS. 27A and 27B is a cross section of a ring made up of a garter spring 61 and a sleeve 76 that is sealed around the spring. The sleeve is sealed so as to form a fluid-tight channel 78 that surrounds the spring, and which can accept a fluid for dilation of the ring. The ring shown in the figures may be either the inner ring or the outer ring of a retractor according to this embodiment, and those skilled in the art will recognize that the dilation of each occurs in essentially the same manner. In FIG. 27A, the ring is in the undilated state. In this state, the spring 61 defines the outer diameter of the ring. Because the sleeve 76 must be able to expand to the full diameter of a the fully dilated ring, it is sealed to itself at a point that results in a large amount of unfilled space in the channel, so that the sleeve hangs loosely around the spring. Upon dilation of the sleeve channel, however, that space is taken up by the expanded ring, as shown in FIG. 27B. In this state, the outer diameter of the ring is significantly increased, and is defined by the fluid channel itself. The spring 62 resides along an inner surface of the channel, and may be expanded by a radial force from the inner surface of the dilated channel.

Figure 28A:
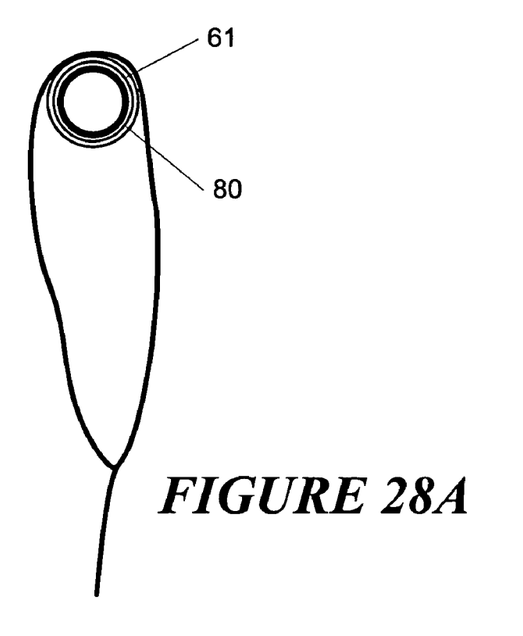
FIGS. 28A and 28B are schematic cross-sectional views of an alternative dilatable ring used with the hydraulically controlled embodiment of the invention shown, respectively, in undilated and dilated states.
Figure 28B:
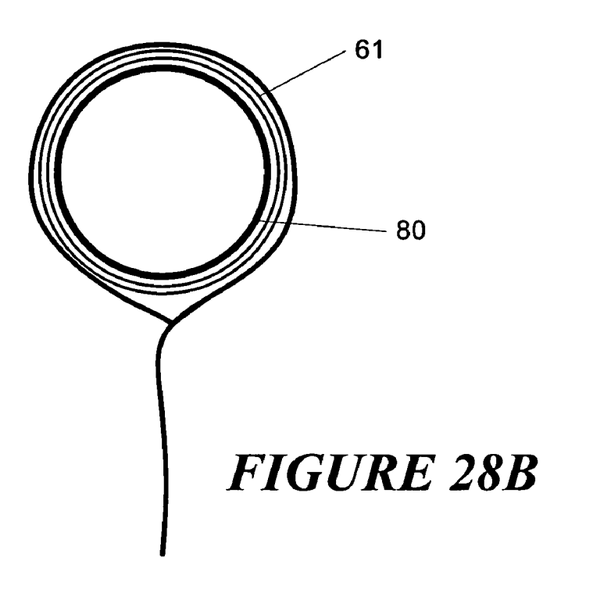

Another variation of the fluid channel is shown in FIGS. 28A and 28B. In this embodiment, the dilatable fluid channel of the ring is formed by a fluid tube 80 that extends into the cavity of the spring 62 itself. In this variation, the pressure in the tube is increased, causing it to expand and, correspondingly, expand the spring 62 outward. The expansion continues until the desired ring diameter is achieved. In this embodiment, although the sleeve itself does not have to include a fluid-tight channel, it does need to have a channel for the spring/tube combination that is large enough to accommodate it at full dilation. Thus, the sleeve still has excess space in its channel in the undilated state shown in FIG. 28A, while in FIG. 28B the expanded spring/tube combination completely fills that space.

The present embodiment may be used with different types of retractors, including those used for obstetrics applications, as described above. Since the dilation of the rings of the retractor serve to open the incision to a desired diameter, the rings themselves would typically have a roughly circular cross-section, as there would be no need to roll the sleeve onto the outer ring. However, those skilled in the art will recognize that the particular cross-sectional shape of the dilatable rings may vary without departing from the operation of this embodiment as described herein. It will also be understood that the drawings herein are not to scale, and that different degrees of dilation may be used to serve different applications. In addition, the overall valve and port structure shown in FIG. 26 is only one example of how to dilate and undilate the rings. Other ways of porting, valving and administering a filling fluid may be used with this embodiment. Likewise, a radial support other than a garter spring may be used with the dilatable ring, provided the desired radial pressure is provided.

Modifications and improvements within the scope of this invention will occur to those skilled in the art. The above description is intended to be exemplary only. The scope of this invention is defined only by the following claims and their equivalents.

What is claimed is:

1. An adjustable retractor, comprising:
   an inner ring having a minimum overall diameter of 20 cm;
   an outer ring spaced from the inner ring and having a minimum overall diameter of 20 cm; and
   an elongate sleeve open at opposite ends, the sleeve extending between the inner and outer rings and being connected at opposite ends to the rings,
   wherein the outer ring is provided with a pre-loaded rotational torque to assist with rotation of the outer ring about its central axis to roll the sleeve about the outer ring to adjust sleeve length.

2. An adjustable retractor according to claim 1 wherein the diameter of the inner and outer rings of the retractor is sufficiently large to allow the passage of a newborn infant therethrough.

3. An adjustable retractor according to claim 1 wherein the inner ring is elastic and may be deformed into an oblong shape for insertion into a surgical incision and is constructed to return to its original shape when released.

4. An adjustable retractor according to claim 3 wherein the inner ring is sufficiently elastic that it may be deformed sufficiently to fit through a surgical incision of 15 cm.

5. A method of retracting the tissue surrounding a surgical incision, the method comprising:
   providing an adjustable retractor comprising an elastic inner ring having a minimum overall diameter of 20 cm, an outer ring spaced from the inner ring and having a minimum overall diameter of 20 cm, and an elongate sleeve open at opposite ends, the sleeve extending between the inner and outer rings and being connected at opposite ends to the rings, wherein the outer ring is provided with a pre-loaded rotational torque to assist with rotation of the outer ring about its central axis to roll the sleeve about the outer ring to adjust sleeve length;
   deforming the inner ring into an oblong shape and inserting it into the surgical incision;
   releasing the inner ring such that it returns to its original shape under skin surrounding the incision; and
   adjusting the length of the sleeve by rotating the outer ring about its central axis with the assistance of the pre-loaded torque to roll the sleeve about itself and the outer ring to adjust sleeve length.

6. A method according to claim 5, wherein the outer ring is formed in a mobius configuration to provide the pre-loaded rotational torque on the outer ring.

7. A method according to claim 5 wherein the surgical incision is part of a caesarean section, and the diameter of the inner and outer rings of the retractor is sufficiently large to allow the passage of a newborn infant therethrough.

8. An adjustable retractor according to claim 5 wherein the surgical incision is approximately 15 cm in length.

9. A method of retracting the tissue for a surgical procedure, the method comprising:
- making an incision no longer than approximately 15 cm;
- providing an adjustable retractor comprising an elastic inner ring having a overall diameter of approximately 25 cm, an outer ring spaced from the inner ring and having an overall diameter of approximately 25 cm, and an elongate sleeve open at opposite ends, the sleeve extending between the inner and outer rings and being connected at opposite ends to the rings
- deforming the inner ring into an oblong shape and inserting it into the surgical incision;
- releasing the inner ring such that it returns to its original shape under skin surrounding the incision; and
- adjusting the length of the sleeve by rotating the outer ring about its central axis with the assistance of the pre-loaded torque to roll the sleeve about itself and the outer ring to adjust sleeve length.

10. A method according to claim 9, wherein the outer ring is provided with a pre-loaded rotational torque to assist with rotation of the outer ring about its central axis to roll the sleeve about the outer ring to adjust sleeve length.

11. A method according to claim 10, wherein the outer ring is formed in a mobius configuration to provide the pre-loaded rotational torque on the outer ring.

12. A method according to claim 9 wherein the surgical incision is part of a caesarean section, and the diameter of the inner and outer rings of the retractor is sufficiently large to allow the passage of a newborn infant therethrough.

13. A method according to claim 9 wherein the surgical incision is part of a caesarean section, and the diameter of the inner and outer rings of the retractor is sufficiently large to allow the passage of a newborn infant therethrough.

14. An adjustable retractor according to claim 9 wherein the surgical incision is approximately 15 cm in length.

15. A method of retracting the tissue for a surgical procedure, the method comprising:
- making an incision no longer than a predetermined incision length;
- providing an adjustable retractor comprising an elastic inner ring having a diameter that is significantly larger than the incision length, such that the incision length is no greater than approximately 60% of the inner ring diameter, an outer ring spaced from the inner ring, and an elongate sleeve open at opposite ends, the sleeve extending between the inner and outer rings and being connected at opposite ends to the rings
- deforming the inner ring into an oblong shape and inserting it into the surgical incision;
- releasing the inner ring such that it returns to its original shape under skin surrounding the incision; and
- adjusting the length of the sleeve by rotating the outer ring about its central axis with the assistance of the pre-loaded torque to roll the sleeve about itself and the outer ring to adjust sleeve length.

16. A method according to claim 15, wherein the outer ring is provided with a pre-loaded rotational torque to assist with rotation of the outer ring about its central axis to roll the sleeve about the outer ring to adjust sleeve length.

17. A method according to claim 16, wherein the outer ring is formed in a mobius configuration to provide the pre-loaded rotational torque on the outer ring.

* * * * *